United States Patent [19]

Sanchez et al.

[11] 4,207,207

[45] Jun. 10, 1980

[54] HYDROCARBON SOLUBLE MAGNESIUM COMPOSITIONS OF HIGH MAGNESIUM CONTENT

[75] Inventors: Ramiro Sanchez, Pasadena; Loyd W. Fannin, Dickinson; Dennis B. Malpass, LaPorte, all of Tex.

[73] Assignee: Texas Alkyls, Inc., Westport, Conn.

[21] Appl. No.: 4,136

[22] Filed: Jan. 17, 1979

[51] Int. Cl.$^2$ .............................................. B01J 31/12
[52] U.S. Cl. ............................. 252/431 R; 260/665 R
[58] Field of Search ................. 252/431 R; 260/665 R

[56]  References Cited
U.S. PATENT DOCUMENTS

| | | | |
|---|---|---|---|
| 3,450,683 | 6/1969 | Hsien et al. | 252/431 R X |
| 3,646,231 | 2/1972 | Kamienski et al. | 252/431 R X |
| 3,704,287 | 11/1972 | Johnson | 252/431 R X |
| 3,737,393 | 6/1973 | De Vries | 252/431 R |
| 4,069,267 | 1/1978 | Kamienski et al. | 252/431 R X |
| 4,127,507 | 11/1978 | Fannin et al. | 252/431 R |

FOREIGN PATENT DOCUMENTS 1251177 10/1971 United Kingdom .

Primary Examiner—Patrick Garvin
Attorney, Agent, or Firm—M. Henry Heines

[57] ABSTRACT

A composition of matter is disclosed comprising dimethylmagnesium, di-n-propylmagnesium and optionally diethylmagnesium. The composition is soluble in aliphatic, cycloaliphatic, and aromatic hydrocarbon solvents without the aid of solubilizing agents. The composition is prepared in the substantial absence of oxygen and moisture by the simultaneous or consecutive reactions of methyl, ethyl, and n-propyl halides with metallic magnesium in the presence of the hydrocarbon solvent, followed by separation of the insoluble magnesium halide and any unreacted magnesium metal from the resulting solution.

27 Claims, No Drawings

HYDROCARBON SOLUBLE MAGNESIUM COMPOSITIONS OF HIGH MAGNESIUM CONTENT

BACKGROUND OF THE INVENTION

Diorganomagnesium compounds are well known for their usefulness in a wide variety of chemical reactions. As reagents, these compounds can be used for the reduction of ketones, the metalation of aromatic compounds and the alkylation of metal halides or oxides to the corresponding metal alkyls. As catalysts, diorganomagnesium compounds are useful in the dimerization and polymerization of olefins, see British Pat. No. 1,251,177, the polymerization of epoxides, see U.S. Pat. No. 3,444,102, and the preparation of telomers, see U.S. Pat. No. 3,742,077. While they perform many of the same types of functions performed by Grignard reagents, diorganomagnesium compounds, owing to differences in electronic and steric factors, are more reactive than Grignard reagents toward certain types of compounds. In general, see also U.S. Pat. Nos. 3,646,231 and 3,822,219.

The utility of diorganomagnesium compounds is lessened by the fact that many are either solids or highly viscous liquids and all are unstable upon exposure to moisture and air. This problem is generally overcome either by dissolving the compound in an inert hydrocarbon solvent or by solvating the compound and by handling under an inert atmosphere. Many diorganomagnesium compounds, particularly those with straight chain lower alkyl groups with a chain length of up to 4 carbon atoms, are insoluble by themselves in hydrocarbon solvents and thus require solubilizing agents which will form a soluble complex. Examples of such solubilizing agents are alkyllithium compounds, see U.S. Pat. No. 3,742,077, dialkyl zinc compounds, see U.S. Pat. No. 3,444,102, alkali metal hydrides, see U.S. Pat. No. 3,655,790, and organoaluminum compounds, see U.S. Pat. Nos. 3,737,393 and 3,028,219.

Solvation involves the use of an ether or an organic base molecule to associate directly with the magnesium atom, thus rendering a liquid-phase complex. The solvated form is undesirable, however, since solvation seriously inhibits the effectiveness of the compound, particularly when the compound is used as a Ziegler-type catalyst. The use of ether is particularly undesirable due to considerations of flammability and explosibility, and because it introduces soluble RMgX according to the Schlenk equilibrium $$R_2Mg + MgX_2 \rightleftarrows 2RMgX$$

where R is alkyl and X is halogen.

Solubilization also serves to reduce the viscosity of reaction mixtures whose high viscosity would otherwise inhibit the progress of the reaction and cause difficulty in handling and transferring. This problem is only partially solved by the use of chloroaryl solvents to form low viscosity suspensions of the insoluble compounds, as described in U.S. Pat. No. 3,264,360.

In addition, the insolubility of the lower alkyl magnesium compounds makes preparation of them in a form free of undesirable halides difficult. In particular, the direct reaction of magnesium metal with an organic halide is disclosed in Glaze and Selman, *Journal of Organometallic Chemistry*, Vol. 5, p. 477 (1967), and W. N. Smith, *Journal of Organometallic Chemistry*, Vol. 64, p. 25 (1974). These articles deal with the preparation of diorganomagnesium compounds with straight chain alkyl groups of 5 carbon atoms and higher. Such compounds are soluble in hydrocarbon solvents and thus readily separable from the concurrently produced magnesium halide and unreacted magnesium. When lower straight chain alkyls are used in this process, the desired diorganomagnesium compound is formed but is insoluble and exists as a slurry in the solvent together with the magnesium halide and unreacted magnesium metal. Thus a solubilizing agent is required when this process is used to make lower alkyl diorganomagnesium compounds. The latter are particularly desirable as reagents and catalysts owing to their relatively high magnesium content on a weight basis.

Other methods of preparation include the mercury-magnesium exchange method, as disclosed in Cowan and Mosher, *Journal of Organic Chemistry*, Vol. 27, p. 1 (1962), and the dioxanate-precipitation method, as disclosed in Schlenk, *Berichte der Deutschen Chemischen Gesselschaft*, Vol. 64, p. 734 (1931). The mercury method, $$R_2Hg + Mg \rightarrow R_2Mg + Hg$$

where R is alkyl, is limited by the high cost of dialkylmercury compounds, and the health hazards involved in their use. The reaction itself is hazardous since it proceeds rapidly and exothermically after an inhibition period.

The dioxanate-precipitation method, $$2RMgX + C_4H_8O_2 \xrightarrow{ether} R_2Mg + C_4H_8O_2 \cdot MgX_2 \downarrow$$

where R is alkyl and X is halogen, involves removal of magnesium halide from ether solutions of Grignard reagents by precipitation of a complex which the dioxane forms with the halide. This is a tedious process and results in an etherated dialkylmagnesium complex from which the ether must be removed prior to use of the dialkylmagnesium as a catalyst.

Dialkylmagnesiums can also be prepared from alkyllithiums, see U.S. Pat. No. 3,646,231, by precipitation of lithium halide, $$MgX_2 + 2RLi \rightarrow R_2Mg + 2LiX$$

where R is alkyl and X is halogen. This process is unsuitable for straight-chain lower alkyl diorganomagnesiums which are insoluble in hydrocarbon solvents, since separation of the diorganomagnesium from the product mixture is impossible. The use of basic solvents renders separation possible but requires subsequent desolvation.

Also disclosed in the same reference is the use of a hydrocarbon-soluble diorganomagnesium to solubilize an insoluble diorganomagnesium. The solubilizing members shown in this reference, however, invariably contain branched-chain alkyl groups. Such branched-chain diorganomagnesium compounds cannot be prepared by the Glaze and Selman method mentioned above. This fact is established in the work of Kamienski and Eastham, *Journal of Organic Chemistry*, Vol. 34, p. 1116 (1968). Thus, resort to the lithium halide precipitation method is required. The use of two or more individually insoluble straight-chain diorganomagnesium compounds to mutually solubilize each other has not been disclosed, particularly such compounds which can be prepared by the direct reaction between magnesium metal and alkyl halide.

The general insolubility of dialkylmagnesium compounds with straight-chain lower alkyl groups is thought to be due to intermolecular association resulting in the formation of a polymer-type macro-structure wherein each magnesium atom is tetrahedrally surrounded by four alkyl groups. Known methods of solubilizing these compounds presumably operate to break some of the intermolecular bonds and thereby break down the macro-structure into smaller units. Solvation or complexing as described above are thought to bring about this effect.

Dialkylmagnesium compounds containing either straight-chain alkyl groups of five carbon atoms or more or branched-chain alkyl groups of any length are also known to be effective as solubilizing agents. Similar to other solubilizing agents, these compounds are thought to bring about the solubilizing effect by breaking the intermolecular bonds of the polymer-type structure. With alkylmagnesium compounds, however, the effect is thought to occur by way of alkyl interchange and re-association, whereby the solubilizing alkyl groups exchange positions with some of the straight-chain lower alkyl groups. Polymerization is thus sterically hindered, either because the substituted groups are unwieldy for a tetrahedral fit around the magnesium atom, or because the groups have some inherent solubility of their own.

Thus, it is surprising that certain independently insoluble and presumably polymer-forming dialkylmagnesium compounds can be combined to form a hydrocarbon-soluble composition. Stated differently, it is surprising and unexpected that alkyl interchange between dimethylmagnesium, diethylmagnesium, and di-n-propylmagnesium is sufficient to break down the intermolecular bonds and render a soluble mixture. This theory of alkyl interchange is offered merely to show the unexpected nature of the composition of the present invention, and is intended neither to define nor to limit the invention in any manner.

It is therefore an object of the present invention to provide hydrocarbon-soluble diorganomagnesium compositions of high magnesium content.

A further object of the present invention is to provide a process by which hydrocarbon soluble diorganomagnesium compositions of high magnesium content can be prepared by the direct reaction of alkyl halides with magnesium.

A still further object of the present invention is to provide a means for solubilizing straight chain lower alkyl diorganomagnesium compounds in hydrocarbon solvents.

Further objects will be apparent from the following description.

BRIEF DESCRIPTION OF THE INVENTION

It has now been discovered that a composition of matter comprising dimethylmagnesium and di-n-propylmagnesium is soluble in hydrocarbon solvents, without the aid of a solubilizing agent. It has further been discovered that a composition of matter comprising dimethylmagnesium, diethylmagnesium, and di-n-propylmagnesium is soluble in hydrocarbon solvents, without the aid of a solubilizing agent. None of these compounds is soluble alone.

Related to these discoveries is the discovery that a hydrocarbon solution mixture of either of these two compositions can be prepared by direct reaction between metallic magnesium and each of the corresponding alkyl halides added in consecutive or simultaneous manner to the same vessel in the presence of the solvent.

This discovery is in contrast to the known behavior of these compounds. When separately prepared by the reaction between metallic magnesium and the appropriate alkyl halide, the compounds are insoluble. Their solid form renders them inseparable from both the concurrently formed magnesium halide and any unreacted magnesium metal remaining in the vessel. The present invention thus provides a novel method for the preparation of straight-chain lower alkyl diorganomagnesium compounds in hydrocarbon solution substantially free of halides and metallic magnesium without the use of solubilizing agents or solvation.

DETAILED DESCRIPTION OF THE INVENTION

According to the present invention, either dimethylmagnesium and di-n-propylmagnesium or dimethylmagnesium, dimethylmagnesium, and di-n-propylmagnesium are combined to provide a composition which is soluble in hydrocarbon solvents.

The term "hydrocarbon solvent" is used herein to designate aliphatic, cycloaliphatic, and aromatic hydrocarbons. Illustrative of aliphatic solvents are n-pentane, iso-pentane, n-hexane, n-heptane, n-octane, isooctane, pentamethylheptane, and gasoline and other petroleum fractions. Illustrative of cycloaliphatic solvents are cyclohexane, methylcyclohexane, methylcyclopentane; cycloheptane, and cyclooctane. Illustrative of aromatic solvents are benzene, toluene, xylene, ethylbenzene, tetralin, and α-methylnaphthalene. Preferred solvents are those containing 5 to 20 carbon atoms, inclusive. More preferred are those containing 6 to 15 carbon atoms, inclusive. Particularly preferred solvents are those which have boiling points between about 69° C. and about 110° C.

As indicated above, it is known in the art of dialkylmagnesium compounds that mixing a soluble dialkylmagnesium with an insoluble dialkylmagnesium will tend to render the latter soluble in hydrocarbons. In analogous manner, the ternary composition of the present invention can be used as a solubilizing agent for an otherwise insoluble dialkylmagnesium, such as di-n-butylmagnesium. Thus, the scope of the present invention is intended to include compositions containing all four alkyl group lengths, ranging from one to four carbon atoms each.

The concentration of dialkylmagnesium in the solvent is not critical and the compounds are soluble over a wide range of concentration. The solution viscosity increases with concentration, however. Therefore, the preferred dialkylmagnesium concentration is from about 0.2 to about 12.0 weight percent, most preferably from about 1.0 to about 5.0 weight percent in terms of magnesium.

The solution can be prepared by physically combining the individual solid dialkylmagnesium compounds with the hydrocarbon solvent. Solubilization can be hastened by heating the resulting mixture to a temperature of about 50° C. or higher. The rate of solubilization increases as the temperature is raised. A clear solution results which is readily separable from any insolubles retained with the compounds. Once the compounds are dissolved, they will remain in solution upon any subsequent lowering of temperature.

If desired, separation of the solution from the remaining undissolved solids can be enhanced by the use of viscosity reducing agents of which a wide variety are known in the art. Organoaluminum compounds are particularly useful in this regard. Trialkylaluminums, dialkylaluminum halides, and alkylaluminum dihalides are examples. These compounds can also be generated in situ from aluminum chloride. Aluminum alkoxides, bis-oxides, and hydrides are also effective.

Alternatively, the dialkylmagnesium compounds can be prepared directly in the solvent in a common vessel by either simultaneous or subsequent reactions. Any reaction is suitable in which neither the by-products nor the unreacted starting materials are soluble in the final mixture. The insolubles can thus be easily filtered off. One such technique involves the direct reaction between metallic magnesium and each of the alkyl halides. The concurrently produced magnesium chloride forms a precipitate which is readily removed from the solution together with any unreacted magnesium still present. Another technique involves the use of a Grignard reagent, preferably methyl magnesium chloride, to supply the methyl group. The Grignard reagent is preferably freed of all ether used in its preparation prior to its use in the present reaction. The desired solution is then obtained by combining the desolvated methyl Grignard reagent with the product obtained from the reaction between magnesium metal and an n-propyl halide, or in the case of the three-way combination, an ethyl halide and an n-propyl halide.

Following any of the above procedures, the solids can be removed from the reaction mixture by any conventional technique, for example, centrifuging, decanting, or filtration. The resulting solution can then be diluted or concentrated to achieve the desired concentration.

With regard to the dimethylmagnesium/di-n-propylmagnesium combination, the mutual solubilizing effect is achieved at a methyl:n-propyl mole ratio of from about 0.2:1 to about 5:1. The preferred range of mole ratio is from about 0.5:1 to about 2:1. Generally, the mutual solubilizing effect is not complete and a quantity of either or both of the two compounds remains undissolved.

With regard to the dimethylmagnesium/diethylmagnesium/di-n-propylmagnesium combination, the mutual solubilizing effect is achieved when the relative quantities of the three dialkylmagnesium compounds are as follows: approximately 10 to 80 mole percent dimethylmagnesium, approximately 10 to 80 mole percent diethylmagnesium, and approximately 10 to 80 percent di-n-propylmagnesium, all stated as percentages of the toal dialkylmagnesium content, excluding the solvent quantity.

In a preferred embodiment, the relative quantities are as follows: approximately 10 to 60 mole percent dimethylmagnesium, approximately 20 to 70 mole percent diethylmagnesium, and approximately 20 to 70 mole percent di-n-propylmagnesium.

In a further preferred embodiment, the relative quantities are as follows: approximately 10 to 30 mole percent dimethylmagnesium, approximately 35 to 55 mole percent diethylmagnesium, and approximately 35 to 55 mole percent di-n-propylmagnesium.

When magnesium is reacted directly with an alkyl halide, commercial grade magnesium turnings or shavings can be used. It is preferable, however, to use higher surface area forms of the metal. While the surface area can be increased by milling, the use of finely divided magnesium powder is most preferred, with a particle size equal to or less than about 150 microns. This form of the metal serves to enhance the reaction rate and minimize the occurrence of Wurtz coupling reactions.

When the reactions between metallic magnesium and each of the alkyl halides are done in the same vessel, they may be performed simultaneously, in any order of succession, or in any combination. It is noted, however, that reactivity increases with increasing alkyl chain length. Thus, the n-propyl halide reacts much more readily with magnesium than the methyl or ethyl halide. This is significant since an uncontrolled reaction can cause coating of the unreacted magnesium particles with solid dialkylmagnesium, seriously inhibiting further reaction. Thus, when the n-propyl halide reaction is performed first, special care must be taken to avoid this problem. A large amount of solvent, extra agitation, a slow rate of n-propyl halide addition, or the further addition of excess magnesium are helpful in this regard.

A preferred method of performing these reactions is to do them in succession, using the ethyl halide first, the n-propyl halide second, and the methyl halide last. The slow reaction rate of the ethyl halide relative to the n-propyl halide provides improved control when this order is used. In practical application, a magnesium activating agent is used to initiate the ethyl halide reaction. The term "magnesium activating agent" is used herein to denote heat or any substance which, when contacted with magnesium, will cause the reaction to occur at a substantially faster rate. Many activating agents are known in the art. Typical examples are $AlCl_3$, $AlCl_3$-ether complexes, N,N-dimethylaniline, molecular iodine, alkyl halides of at least three carbon atoms, Grignard reagents, and dialkylmagnesium with alkyl groups of at least three carbon atoms. Thus, a small quantity of n-propyl halide can serve as an activating agent.

Thermal activation is the preferred method for the ethyl halide reaction and is generally achieved at temperatures between about 125° C. and about 350° C., preferably from about 150° C. to about 250° C., and most preferably from about 150° C. to about 200° C. Once the magnesium is activated, the magnesium/ethyl halide reaction can proceed at lower temperatures. Although reaction can occur over a wide temperature range once the magnesium is activated, it will be most convenient to operate between about 20° C. and about 200° C., preferably between about 50° C. and about 175° C., and most preferably between about 100° C. and about 150° C. At least 10% by weight of alkyl halide based on the weight of magnesium metal must be present during thermal activation.

Activation of the magnesium is normally required for the methyl halide reaction as well. When the preferred reaction order is used, however, the use of heat or an additional substance is unnecessary, since activation is supplied by the reaction product of the n-propyl halide reaction.

The remaining reactions are also operable over a wide temperature range, but are most conveniently run at a temperature between about 50° C. and about 200° C., preferably between about 80° C. and about 140° C.

When only the methyl and n-propyl halides are used, it is preferably to react all or a substantial portion of the n-propyl halide first. As indicated above, control of the reaction can be enhanced by a slow rate of addition. The n-propyl halide further serves as an activating agent for the methyl halide reaction. Alternatively, as with the ethyl halide reaction, other means of activation or initiation will improve the progress of the methyl halide reaction.

The temperature ranges quoted above are not critical. For the most part, they are subject only to practical considerations. The minimum temperature is dictated largely by process economics, while the maximum temperature is limited only by the possibility of alkyl halide decomposition and consideration of energy conservation.

The term "halide" as used herein denotes chloride, bromide, or iodide, or combinations thereof. Chlorides are generally preferred for reasons of economy. Usually, a small amount of halide is present in the final product solution. This can be minimized by the use of chlorides rather than iodides or bromides, since the amount of soluble halide observed decreases in the order I>Br>Cl.

The reactant mole ratio can be varied over a wide range. No particular range is critical to the performance of any of the reactions. Normally, however, the starting materials will be such that the mole ratio of magnesium to total halides is from about 1.0 to about 2.0, preferably from about 1.1 to about 1.3. The excess magnesium inherent in mole ratios greater than 1.0 is effective in minimizing Wurtz coupling reactions.

The hydrocarbon solvent may be added before, during, or after the reaction. It will be most convenient to add the solvent prior to or during the first reaction, so that further reaction is not inhibited by high viscosity.

Magnesium alkyls are pyrophoric substances, capable of spontaneous ignition upon contact with air. To prevent such ignition, and also to prevent oxidation of the metallic magnesium, the reactions must be carried out in the absence of more than trace amounts of oxygen. Thus, the reactions are normally carried out in an atmosphere of inert gas such as nitrogen or argon, or in an atmosphere of methyl or ethyl halide gas. The reactions must also be conducted in the substantial absence of water, due to the susceptibility of the system components to decomposition in the presence of water.

The pressure under which the reactions are conducted is not critical and pressures ranging from atmospheric to elevated pressures of several atmospheres can be employed. The methyl halide reaction will be most conveniently run at least in slight excess of atmospheric in order to keep the methyl halide in solution. The preferred pressure range is about 8 pounds per square inch gauge (psig) [5.5 Newtons per square centimeter in excess of atmospheric ($N/cm^2$)] to about 100 psig (69 $N/cm^2$). Lower pressures can be used with the n-propyl halide reaction.

The present invention is further illustrated by the following examples.

Of these examples, the first two illustrate the preparation of a heptane solution containing dimethylmagnesium and di-n-propylmagnesium. These examples differ only in the final concentration of soluble magnesium in the product solution.

EXAMPLE 1

Methyl-n-Propyl Combination

A 12-ounce pressure bottle fitted with a thermowell, variable diptube, and magnetic stirring bar was immersed in an oil bath, and charged with 15.0 g (0.617 g-atom) of 100-mesh magnesium powder and 210 g of n-heptane under a nitrogen atmosphere. With constant stirring, the resulting slurry was heated to 124° C. with the oil bath and a small amount of n-propyl chloride was added. A temperature rise was observed in the bottle, indicating initiation of the reaction. When the temperature of the reaction mixture returned to the level of the bath temperature, further n-propyl chloride was added. Over a 90-minute period, the total n-propyl chloride charge was 7.0 g (0.0891 mole). The bath temperature was then raised to 147° C. and methyl chloride was added in increments over a 60-minute period to a total methyl chloride charge of 5.20 g (0.103 mole).

The reaction bottle was then removed from the bath and stirring was ceased. When the solution had cooled and the solids had settled, a sample was taken of the viscous solution. While contact with air was still avoided, the sample was degassed and analyzed, the results indicating 0.68 weight percent magnesium and 0.10 weight percent chloride in soluble form. The quantity of soluble magnesium corresponds to 63% theoretical yield. A sample of the solution was then hydrolyzed to determine the relative amounts of the alkyl groups from the hydrolysis gas composition. The hydrolysis gas contained 53 mole percent methane and 42 mole percent propane. These percentages correspond directly to the relative amounts of methyl and n-propyl groups in solution.

EXAMPLE 2

Methyl/n-Propyl Combination

The pressure bottle described in Example 1 was charged with 6.1 g (0.251 g-atom) of 100-mesh magnesium powder. At a bath temperature of 120° C., a small amount of n-propyl chloride was added to the dry metal and a temperature rise was observed in the bottle. The bottle was then cooled to ambient temperature and 30 g of n-heptane was added. The temperature was then raised to 99° C. and n-propyl chloride was added incrementally over a 35-minute period to a total n-propyl chloride charge of 3.0 g (0.0382 mole). The reaction temperature was then raised to 130° C. and 6.0 g (0.119 mole) of methyl chloride was added over a 120-minute period. Following the methyl chloride addition, the temperature was lowered to 120° C. and 4.6 g (0.0586 mole) of additional n-propyl chloride was added over a 105-minute interval.

The solution was then cooled to ambient temperature and the solids were allowed to settle. A sample was taken while contact with air was avoided. Analysis of the sample showed 1.24 weight percent soluble magnesium (corresponding to 18% theoretical yield based on the limiting n-propyl chloride charge) and 0.19 weight percent soluble chloride. The hydrolysis gas contained 53 mole percent methane and 46 mole percent propane.

The product solution was then concentrated by evaporation to give a solution containing 1.80 weight percent soluble magnesium.

The next two examples illustrate the preparation of a heptane solution of dimethylmagnesium, diethylmagnesium, and di-n-propylmagnesium. In each case, the first reaction performed is that between metallic magnesium and ethyl chloride, with the aid of di-n-hexylmagnesium as a magnesium activating agent.

EXAMPLE 3

Methyl/Ethyl/n-Propyl Combination

The pressure bottle described in Example 1 was charged with 10.0 g (0.411 g-atom) of 100-mesh magnesium powder, 100 g of n-heptane, and 0.08 g of di-n-hexylmagnesium as a 12.7 weight percent solution in n-heptane, under a nitrogen atmosphere. The resulting slurry was heated to 109° C., and ethyl chloride was added in increments to a total ethyl chloride charge of 7.5 g (0.116 mole). After maintaining a temperature of 108° C. for two hours in the reaction mixture, addition of n-propyl chloride was begun. Over a period of one hour, 7.50 g (0.095 mole) of n-propyl chloride was added. The reaction bottle was then cooled to ambient temperature and evacuated. The reaction mixture was then heated to 124° C. and addition of methyl chloride was begun. Increments of methyl chloride were added to the reaction bottle until the pressure had risen to 52 psig (36 N/cm$^2$). The reactor was then cooled once more to ambient temperature, evacuated, and reheated to 132° C. Methyl chloride addition was resumed until a reactor pressure of 56 psig (39 N/cm$^2$) was achieved, bringing the total methyl chloride charge to 3.03 g (0.061 mole). The bottle was then cooled to 60° C. and the solids were allowed to settle.

The solution was sampled and analyzed as in Examples 1 and 2, the results indicating 0.61 weight percent soluble magnesium (24% theoretical yield) and 0.016 weight percent soluble chloride. The hydrolysis gas contained 21 mole percent methane, 37 mole percent ethane, and 39 mole percent n-propane.

EXAMPLE 4

Methyl/Ethyl/n-Propyl Combination

The pressure bottle described in Example 1 was charged with 13.0 g (0.535 g-atom) of 100-mesh magnesium powder, 132 g of n-heptane, and 0.23 g of di-n-hexylmagnesium as a 12.7% solution in n-heptane. Ethyl chloride was added incrementally at 97° C. to a total ethyl chloride charge of 11.0 g (0.17 mole). An equal number of moles of n-propyl chloride was then added at 102° C. The temperature of the reaction was then raised to 126° C. and methyl chloride was added in increments until an increase in solution viscosity was noticed. The total methyl chloride charge was approximately 2.0 g (0.04 mole). The bottle and its contents were then cooled and the solids were allowed to settle. Analysis of the resulting solution indicated 0.83 weight percent magnesium, corresponding to approximately 25% yield, and 1.14 weight percent chloride. The hydrolysis gas contained 12% methane, 39% ethane, and 45% propane.

What is claimed is:

1. A hydrocarbon-soluble composition of matter comprising dimethylmagnesium and di-n-propylmagnesium at a methyl:n-propyl alkyl group ratio of from about 0.2:1 to about 5:1.

2. A composition according to claim 1 in which the methyl:n-propyl alkyl groups ratio is from about 0.5:1 to about 2:1.

3. A hydrocarbon-soluble composition of matter comprising dimethylmagnesium, diethylmagnesium, and di-n-propylmagnesium, in which the relative amounts of the dialkylmagnesium compounds are
   (a) approximately 10 to 80 mole percent dimethylmagnesium,
   (b) approximately 10 to 80 mole percent diethylmagnesium, and
   (c) approximately 10 to 80 mole percent di-n-propylmagnesium.

4. A composition according to claim 3 comprising
   (a) approximately 10 to 60 mole percent dimethylmagnesium,
   (b) approximately 20 to 70 mole percent diethylmagnesium, and
   (c) approximately 20 to 70 mole percent of di-n-propylmagnesium.

5. A composition according to claim 3 comprising
   (a) approximately 10 to 30 mole percent dimethylmagnesium,
   (b) approximately 35 to 55 mole percent diethylmagnesium, and
   (c) approximately 35 to 55 mole percent di-n-propylmagnesium.

6. A composition of matter comprising the components
   (a) dimethylmagnesium,
   (b) di-n-propylmagnesium, and
   (c) a solvent selected from the group consisting of aliphatic, cycloaliphatic and aromatic hydrocarbons containing 5 to 20 carbon atoms, inclusive, components (a) and (b) being present in quantities relative to each other such that the methyl:n-propyl mole ratio is between about 0.2:1 and about 5:1.

7. A composition according to claim 6 in which the methyl:n-propyl alkyl group ratio is from about 0.5:1 to about 2:1.

8. A composition according to claim 6 further comprising diethylmagnesium, in which the relative amounts of the dialkylmagnesium compounds are
   (a) approximately 10 to 80 mole percent dimethylmagnesium,
   (b) approximately 10 to 80 mole percent diethylmagnesium, and
   (c) approximately 10 to 80 mole percent di-n-propylmagnesium.

9. A composition according to claim 8 in which the relative amounts of the dialkylmagnesium compounds are
   (a) approximately 10 to 60 mole percent dimethylmagnesium,
   (b) approximately 20 to 70 mole percent diethylmagnesium, and
   (c) approximately 20 to 70 mole percent di-n-propylmagnesium.

10. A composition according to claim 8 in which the relative amounts of the dialkylmagnesium compounds are
    (a) approximately 10 to 30 mole percent dimethylmagnesium,
    (b) approximately 35 to 55 mole percent diethylmagnesium, and
    (c) approximately 35 to 55 mole percent di-n-propylmagnesium.

11. A composition according to claim 6, 7, 8, 9, or 10 in which the solvent is a member selected from the group consisting of aliphatic, cycloaliphatic, and aromatic hydrocarbons containing 6 to 15 carbon atoms, inclusive.

12. A composition according to claim 6, 7, 8, 9, or 10 in which the solvent is a member selected from the group consisting of aliphatic, cycloaliphatic, and aromatic hydrocarbons which have boiling points between about 69° C. and about 110° C.

13. A composition according to claim 6, 7, 8, 9, or 10 in which the concentration of dialkylmagnesium in the solvent is from about 0.2 weight percent to about 12 weight percent in terms of magnesium.

14. A composition according to claim 6, 7, 8, 9, or 10 in which the concentration of dialkylmagnesium in the solvent is from about 1 weight percent to about 5 weight percent in terms of magnesium.

15. A process for the manufacture of a hydrocarbon solution of a dialkylmagnesium composition which comprises
   (a) reacting metallic magnesium with a methyl halide and a n-propyl halide, either simultaneously or in any order of succession, in a common vessel in the presence of a hydrocarbon solvent, to produce a homogeneous liquid and solids, and
   (b) separating said homogeneous liquid from said solids, both steps being conducted in the substantial absence of both moisture and oxygen.

16. A process for the manufacture of a hydrocarbon solution of a dialkylmagnesium composition which comprises
   (a) reacting metallic magnesium with a methyl halide, an ethyl halide, and a n-propyl halide, either simultaneously or in any order of succession, in a common vessel in the presence of a hydrocarbon solvent, to produce a homogeneous liquid and solids, and
   (b) separating said homogeneous liquid from said solids, both steps being conducted in the substantial absence of both moisture and oxygen.

17. A process according to claim 15 or 16 in which the hydrocarbon solvent is a member selected from the group consisting of aliphatic, cycloaliphatic, and aromatic hydrocarbons containing 5 to 20 carbon atoms, inclusive.

18. A process according to claim 15 or 16 in which the hydrocarbon solvent is a member selected from the group consisting of aliphatic, cycloaliphatic and aromatic hydrocarbons containing 6 to 15 carbon atoms, inclusive.

19. A process according to claim 15 or 16 in which the hydrocarbon solvent is a member selected from the group consisting of aliphatic, cycloaliphatic, and aromatic hydrocarbons which having boiling points between about 69° C. and about 110° C.

20. A process according to claim 15 or 16 in which the magnesium metal is in the powdered state.

21. A process according to claim 15 or 16 in which the magnesium metal is comprised of particles of diameter equal to or less than about 150 microns.

22. A process according to claim 15 or 16 in which the mole ratio of magnesium to total halides is between about 1.0 and about 2.0.

23. A process according to claim 15 or 16 in which the mole ratio of magnesium to total halide is between about 1.1 and about 1.3.

24. A process according to claim 15 or 16 in which all halides are chlorides.

25. A process according to claim 16 in which the reactions of step (a) are performed in succession in the order ethyl—propyl—methyl, and the magnesium is activated by a magnesium activating agent either prior to or during the ethyl halide reaction.

26. A process according to claim 25 in which the magnesium is thermally activated at a temperature between about 125° C. and about 350° C.

27. A process according to claim 25 in which the magnesium activating agent is a soluble dialkylmagnesium compound.

* * * * *

UNITED STATES PATENT AND TRADEMARK OFFICE
CERTIFICATE OF CORRECTION

PATENT NO. : 4,207,207
DATED : June 10, 1980
INVENTOR(S) : Ramiro Sanchez et al.

It is certified that error appears in the above-identified patent and that said Letters Patent are hereby corrected as shown below:

Column 1, line 40 — the number "3,028,219" should read —3,028,319—.

Column 4, line 22 — the word "dimethylmagnesium" should read —diethylmagnesium—.

Column 5, line 53 — the word "toal" should read —total—.

Signed and Sealed this

Fourteenth Day of April 1981

[SEAL]

Attest:

RENE D. TEGTMEYER

Attesting Officer

Acting Commissioner of Patents and Trademarks